(12) United States Patent
Heid

(10) Patent No.: US 12,285,291 B2
(45) Date of Patent: Apr. 29, 2025

(54) ULTRASONIC SYSTEM AND IMAGING ULTRASONIC METHOD

(71) Applicant: H-NEXT GMBH, Erlangen (DE)

(72) Inventor: Oliver Heid, Erlangen (DE)

(73) Assignee: H-NEXT GMBH, Erlangen (DE)

( * ) Notice: Subject to any disclaimer, the term of this patent is extended or adjusted under 35 U.S.C. 154(b) by 410 days.

(21) Appl. No.: 17/760,799

(22) PCT Filed: Aug. 20, 2020

(86) PCT No.: PCT/EP2020/073367
§ 371 (c)(1),
(2) Date: Mar. 16, 2022

(87) PCT Pub. No.: WO2021/052705
PCT Pub. Date: Mar. 25, 2021

(65) Prior Publication Data
US 2022/0378401 A1 Dec. 1, 2022

(30) Foreign Application Priority Data
Sep. 16, 2019 (DE) .......................... 102019124811.6

(51) Int. Cl.
*A61B 8/00* (2006.01)
*G01S 7/52* (2006.01)
(Continued)

(52) U.S. Cl.
CPC ............ *A61B 8/4444* (2013.01); *A61B 8/565* (2013.01); *G01S 7/52023* (2013.01);
(Continued)

(58) Field of Classification Search
None
See application file for complete search history.

(56) References Cited

U.S. PATENT DOCUMENTS 5,689,507 A 11/1997 Bloks
9,842,075 B1 * 12/2017 Davis .................. G06F 13/4295
(Continued)

FOREIGN PATENT DOCUMENTS

| CN | 102594640 A | 7/2012 |
| CN | 103412518 A | 11/2013 |

(Continued)

OTHER PUBLICATIONS

International Search Report for PCT/EP2020/073367 (Nov. 24, 2020).

(Continued)

*Primary Examiner* — Isam A Alsomiri
*Assistant Examiner* — Jonathan D Armstrong
(74) *Attorney, Agent, or Firm* — Merchant & Gould P.C.

(57) ABSTRACT

An ultrasonic system includes an ultrasonic probe and a data processing unit which is physically separate from the ultrasonic probe, runs on an operating system and has a receiving memory and a transmission memory. A real-time bus system is for data coupling of the ultrasonic probe to the memories. A probe system manages data within the ultrasonic probe, the clock inaccuracy of the probe system is at least three orders of magnitude less than the clock inaccuracy of the real-time bus system. The response time of the operating system is at least two orders of magnitude longer than the clock inaccuracy of the real-time bus system. The real-time bus system is configured to transfer transmission data and received data simultaneously by uninterrupted streaming clocked with an on average constant rate during stateless operation of the ultrasonic probe, the operation not differentiating between transmission and receiving operation.

16 Claims, 2 Drawing Sheets

(51) Int. Cl.
*G06F 13/28* (2006.01)
*G06F 13/42* (2006.01)

(52) U.S. Cl.
CPC .......... *G06F 13/28* (2013.01); *G06F 13/4221* (2013.01); *G06F 2213/0026* (2013.01)

(56) References Cited

U.S. PATENT DOCUMENTS

| | | | | |
|---|---|---|---|---|
| 9,996,484 | B1* | 6/2018 | Davis | G06F 13/105 |
| 10,452,570 | B1* | 10/2019 | Liguori | G06F 9/45558 |
| 11,868,301 | B1* | 1/2024 | Frink | G06F 13/4022 |
| 2008/0110266 | A1 | 5/2008 | Randall et al. | |
| 2008/0151765 | A1 | 6/2008 | Cheruvathery | |
| 2008/0294046 | A1 | 11/2008 | Chiang et al. | |
| 2009/0006708 | A1* | 1/2009 | Lim | G06F 13/4022 |
| | | | | 710/314 |
| 2010/0286527 | A1 | 11/2010 | Cannon | |
| 2012/0177059 | A1 | 7/2012 | Jiang et al. | |
| 2013/0079639 | A1 | 3/2013 | Hoctor et al. | |
| 2014/0058266 | A1 | 2/2014 | Call et al. | |
| 2014/0237156 | A1* | 8/2014 | Regula | G06F 13/4022 |
| | | | | 710/314 |

FOREIGN PATENT DOCUMENTS

| | | |
|---|---|---|
| CN | 103908304 A | 7/2014 |
| DE | 102011006827 A1 | 10/2012 |
| DE | 102018203444 A1 | 9/2019 |
| EP | 0762142 B1 | 7/2001 |
| EP | 2614775 A1 | 7/2013 |
| EP | 3117774 B1 | 1/2019 |
| EP | 2627257 B1 | 4/2019 |
| JP | 2000163364 A | 6/2000 |
| WO | 2010/127917 A1 | 11/2010 |
| WO | 2019123458 A1 | 6/2019 |

OTHER PUBLICATIONS

Chinese Search Report received for CN Application No. 202080064528.9, 3 pgs.

* cited by examiner

ULTRASONIC SYSTEM AND IMAGING ULTRASONIC METHOD

This application is a National Stage Application of PCT/EP2020/073367 filed Aug. 20, 2022, which claims benefit of Ser. No. 10/2019124811.6, filed Sep. 16, 2019, in Germany, and which applications are incorporated herein by reference. To the extent appropriate, a claim of priority is made to each of the above disclosed applications.

BACKGROUND OF THE INVENTION

The invention relates to an ultrasonic system that can be used in particular as a medical technology system and to an imaging ultrasonic method.

A system and a method for imaging by means of ultrasound is known, for example, from US 2013/0079639 A1. The known ultrasonic system comprises a plurality of electroacoustic transducers which transmit ultrasonic signals and receive echoes of the transmitted ultrasonic signals. The electroacoustic transducers are arranged in a transducer head. Acquired analog signals are digitized, wherein digital raw data are processed further. In order to forward data, a bus system is proposed. Digitized data can be stored and can be stored by a received beam former, inter alia, in order in the end to generate representable ultrasonic images.

An additional ultrasonic system with an ultrasonic probe, that is to say a transducer head, and with a data processing unit spatially separate therefrom, is described in EP 2 614 775 A1. Between the ultrasonic probe and the data processing unit, data is transmitted via a wireless interface.

Known from US 2008/0 110 266 A1 is an ultrasonic system with an ultrasonic probe coupled via a cableless or cabled interface to a computer. The ultrasonic probe has preamplifiers, A/D converters and a buffer memory. Acoustic and synthetic methods are proposed for focusing emitted acoustic signals are proposed. In addition, a synthetic focusing of received ultrasonic signals is provided.

In the case of an ultrasonic system described in US 2008/0 294 046 A1, a transducer head is connected via a cable to a battery-operated evaluation unit.

US 2008/0 110 266 A1 describes an ultrasonic system with an array of sound transducers which are designed as piezoelectric transducers and connected via preamplifiers to analog-digital converters. The digital signals supplied by the analog-digital converters are partially further processed already within the transducer head. Additional digital signal processing occurs in a central unit which is connected by cable or wirelessly to the transducer head.

A storage architecture of an imaging ultrasonic system is described in detail in US 2014/0 058 266 A1. Data to be processed is transferred in this case via a data network.

EP 2 627 257 B1 describes an ultrasonic imaging system with a concavely curved ultrasonic converter arrangement. In the ultrasonic converter arrangement, multiple transmission apertures are located, which deliver unconcentrated ultrasonic pings to a scatterer. A control system is linked to the ultrasonic converters, which enables, inter alia, switching between the different transmission apertures.

EP 3 117 774 B1 discloses a software-based ultrasonic imaging system, within which use is made of a scheme with direct memory access (DMA=direct memory access). Here, a front-end unit of the ultrasonic imaging system is provided for transferring channel data in a DMA scheme.

Known from US 2008/0 151 765 A1 is a ring buffer for preventing jitter in the transfer of audio data. The ring buffer is set up for carrying out mutually independent reading and writing processes.

SUMMARY OF THE INVENTION

The underlying aim of the invention is to further develop imaging by means of ultrasound with respect to the known prior art in particular from the standpoint of efficient and reliable data processing.

This aim is achieved according to the invention by an ultrasonic system having the features of claim 1. The aim is also achieved by an imaging ultrasonic method according to claim 10. Below, designs and advantages of the invention explained in connection with the ultrasonic method also apply as appropriate to the device, that is to say to the ultrasonic system, and vice versa.

The ultrasonic system works with a movable ultrasonic probe, in particular an ultrasonic probe designed as a handheld device, which comprises a plurality of transmitting and receiving elements, and with a data processing unit which is coupled by wire or wireless connection to the ultrasonic probe. In each case, the data processing unit is physically separate from the ultrasonic probe, that is to say spaced apart from the ultrasonic probe without fixed geometric relationship.

In typical designs, a data connection by cable is established between the ultrasonic probe and the data processing unit. The ultrasonic probe in each case comprises a number of transmission end stages, duplexers, analog preamplifiers and analog-digital converters as well as at least one digital connection component, via which the ultrasonic probe is data-coupled to the data processing unit. Data processing, in particular beam forming, on the other hand, is not provided in the ultrasonic probe.

The data processing unit of the ultrasonic system has two memories designed as ring memories, specifically a receiving memory and a transmission memory, which together are also referred to as ring buffer, as well as a computation unit designed for generating ultrasonic images. Here, the ring memories represent components of a real-time bus system (RTS) comprising the ultrasonic probe and the mentioned data connection, in particular a cable. At the same time, the ring memories are incorporated in an operating system, in particular in a standard operating system (BS), existing outside of the real-time bus system (RTS) and provided for operating the computation unit.

A system which manages data within the ultrasonic probe and which is clocked with the aid of a clock generator (clock) built into the ultrasonic probe is referred to as probe system (Son-S). The clock inaccuracy (jitter), that is to say the execution time inaccuracy, of the probe system (Son-S) is at least three orders of magnitude less than the clock inaccuracy (jitter) of the real-time bus system (RTS). This means that the probe system (Son-S) works with a much higher temporal precision than the real-time bus system (RTS). At the same time, the response time of the operating system (BS) of the computation unit is at least two orders of magnitude longer than the clock inaccuracy (jitter) of the real-time bus system. Thus, the response time of the operating system (BS) differs from the clock inaccuracy of the ultrasonic probe by at least a factor of $10^5$. In spite of these five orders of magnitude which each relate to a clock inaccuracy or time difference, images generated by the ultrasonic system are perceived as real-time images. Via the real-time bus system (RTS), transmission data and received data are simultaneously transferred between the ultrasonic probe and the data processing unit spaced apart therefrom by means of uninterrupted streaming clocked with an on average constant rate during stateless operation of the ultrasonic probe, said operation not differentiating between transmission and receiving operation.

Overall, the ultrasonic method according to the invention, in which an object to be examined is exposed to ultrasonic pulses and echo signals are received, has the following features:

provision of an ultrasonic probe which comprises a plurality of transmitting and receiving elements, and of a data processing unit data-coupled to said ultrasonic probe, which comprises a central processor and a processor, in particular a graphics processor, with a plurality of arithmetic units, generation of actuation data provided for operating the transmitting and receiving elements, by the data processing unit, wherein the actuation is generated on a standard operating system which does not meet any hard real-time requirements, and is written asynchronously—with respect to the generation—in a transmission memory designed as memory which is to be included in a real-time bus system, asynchronous—with respect to the generation and the storage of the actuation data—transmission of actuation data from the transmission memory to the ultrasonic probe, wherein the ultrasonic probe is operated as component of the real-time bus system and the actuation data is transmitted with an on average constant first data transfer rate without pause by streaming, and wherein the clock inaccuracy (jitter) of a probe system comprising components within the ultrasonic probe is at least three orders of magnitude less and the response time of the standard operating system is at least two orders of magnitude longer than the clock inaccuracy (jitter) of the real-time bus system, ultrasonic pulses are generated in accordance with the actuation data with the aid of transmission end stages arranged in the ultrasonic probe, wherein the transmitting and receiving elements actuated by the transmission end stages are designed in particular as piezo elements, the associated echo signals are analog amplified and synchronously digitized without interruption and with constant clock frequency, and asynchronously written by means of streaming in real time, uninterrupted, without further processing, via a data connection, in particular a cable, into a receiving memory which is to be included in the real-time bus system and which is spatially separate from the ultrasonic probe and designed as ring memory, wherein the data transfer to the receiving memory occurs uninterrupted with an essentially constant second data transfer rate which deviates by no more than a factor of five, in particular by no more than a factor of two, from the mentioned first data transfer rate relating to the data transfer from the data processing unit to the ultrasonic probe, a selection of data received in the receiving memory is distributed, controlled by the central processor, as measurement data blocks over multiple arithmetic units, wherein the individual measurement data blocks in each case are associated with a group of receiving elements, multiple measurement data sets are processed in parallel and asynchronously with respect to the writing process of the real-time bus system, by arithmetic units which are controlled in each case by the central processor running on the standard operating system, wherein the processing in each case comprises the received beam forming and the image reconstruction, and a partial image is reconstructed with the aid of each arithmetic unit, from the partial images, an overall image is generated by the data processing unit as ultrasonic image to be displayed on a monitor.

Within the ultrasonic probe, a single clock generator (clock) is provided for the transmission end stages as well as for the analog-digital converters.

The invention is based on the consideration that, in the operation of an ultrasonic system which is to be usable in particular in medical technology, there has been a trend to impose increasing demands in terms of the quality of the ultrasonic images which typically represent sectional images. Quality here relates both to the resolution of the images and also to the dimensions of the region which can be acquired by a single ultrasound image, wherein the dimensions include the depth, indicated in cm, for example, of the simultaneously acquired examination region located beneath the ultrasonic probe.

A higher ultrasound image quality is typically associated with a higher rate of data to be transferred and processed. Various physical principles for the signal transfer are conceivable, including, inter alia, an optical signal transfer as described, for example, in EP 0 762 142 B1. In order to limit the rate of data to be transferred between an ultrasonic probe and a separate data processing system, a preliminary processing and a selection of data within the ultrasonic probe is a conceivable way. However, each processing of data in the ultrasonic probe is necessarily associated with energy consumption and thus heat development. In addition, the space requirement of data processing components plays a role. A solution to this dilemma could be sought in a partially analog data processing within the ultrasonic probe, which could also be advantageous from the standpoint of higher real-time requirements.

With the invention, on the other hand, another way is proposed, in that, with regard to both the reception and the transmission of data, the ultrasonic probe is operated in a stateless manner. Transmitting and receiving elements are here continuously adjusted with short clocking cycle of, for example, 8 ns, to a respective current state. A continuation of this state, as long as no new adjusting occurs, is not provided. Rather, with each clock pulse, in the mentioned example every 8 ns, a state is set anew, wherein said state can be identical to the previous state or represent a different state. Thereby, on the one hand, the data processing effort, as far as the complexity of the processing is concerned, in the ultrasonic probe is minimized, and, on the other hand, the risk of continuation of an incorrect setting during ongoing operation is eliminated. When the ultrasonic system is switched on and when the data connection between the ultrasonic probe and the data processing unit is broken, the transmitting and receiving elements assume a safe state, if said safe state does not already exist in any case. The very high data rate associated with the stateless operation of the transmitting and receiving elements is acceptable.

Already during the analog processing of the received data, that is to say ultrasonic echoes, in the ultrasonic system, the effort can be minimized in comparison to conventional solutions in that the preamplifiers are operated with constant amplification (gain). This means that there is no dependence of the preamplification on the distance from a structure triggering an echo to the transmitting and receiving element.

Thus, in the case of a pixel with the shortest distance from the transmitting and receiving element, the same amplification is used as for pixels with maximum distance from the transmitting and receiving element.

In spite of very high continuous data rates with regard to both data transfer to the ultrasonic probe and data transfer from the ultrasonic probe to the evaluation unit, the elimination of data processing within the ultrasonic probe to a large extent enables a design of the ultrasonic probe as handheld device with reduced heat development, which can be managed without particular cooling measures.

In a preferred embodiment, the transmitting and receiving elements of the ultrasonic probe are combined transmitting and receiving elements, that is to say elements which take on both the transmission function and the receiving function. In particular, piezo elements are suitable for this purpose.

As far as the number and the geometric arrangement of the transmitting and receiving elements, in particular piezo elements, within the ultrasonic probe are concerned, various embodiments can be implemented. For example, 128 piezo elements of basically known design are arranged in a line.

In a preferred embodiment, upstream of each transmitting and receiving element, a duplexer is connected, which is designed for the clocked application of one of n codes to the transmitting and receiving element for in each case exactly one cycle, wherein n is at least four, and (n−1) transmission codes and in addition exactly one reception code are provided. In the case of three transmission codes, for example, one of these transmission codes corresponds to a positive voltage value, and another transmission code corresponds to a negative voltage value of equal amount, and the third transmission code corresponds to a voltage of zero. The coding in this case can occur by a 2 bit signal. In spite of the very short clock pulse of, for example, 8 ns, the data transfer rate thus remains in a range which can be managed with acceptable effort. With a higher number of bits, the setting of intermediate values of the voltage to be applied to a transmitting and receiving element is theoretically also possible. In each case, each transmission-reception state becomes active and is maintained for the length of only one clock pulse. In case of error, an automatic default safety switch-off occurs, that is to say an assumption of a safe default state.

In an advantageous embodiment, within the data processing unit, there is a root complex, via which the real-time bus system establishes a connection to the ultrasonic probe. The root complex is used, inter alia, for the transfer of message data packets (MSI) which relate to transmission data and received data, wherein, by the message data packets (MSI), counting semaphores are implemented for temporarily blocking and releasing the streaming data transfer into the transmission memory and out of the receiving memory. The data transfer capacity kept available for the transfer of message data packets (MSI) is preferably no more than in each case 1% of the data transfer capacities provided for transferring, on the one hand, actuation data and, on the other hand, measurement data via the data connection.

Three time domains are given by the operating system (BS) of the computation unit, the real-time bus system (RTS) and the probe system (Son-S), which—in the mentioned sequence of the systems—meet increasing real-time requirements. For example, between the temporal jitter (TSon) of the probe system (Son-S), the jitter (TBus) of the real-time bus system (Bus-S) and the response time (TBS) of the operating system (BS), the following relationship exists:

$$10^1 \leq \frac{TBus^2}{TSoN * TBS} \leq 10^4$$

In particular, the mentioned dimensionless fraction $TBus^2/(TSon \times TBS)$ has a value of at least 100 and at most 10,000.

The received data memory into which data is written via the real-time bus system (Bus-S) and from which data is read for processing on the operating system (BS), in particular standard operating system, is preferably designed to store received data blocks which are associated with transmission data sets, for at least 20 ms. Here, the transmission data stream is provided for the continuous, uninterrupted actuation of the transmitting and receiving elements, wherein the associated received data stored in the transmission and receiving memories is stored temporally uninterrupted, sequentially, and without an associated time signal in each individual case. In this manner, time information is passed on implicitly by the size of the stored data blocks and by the sequence of the storage, that is to say the storage address, within the ultrasonic system.

The data connection which couples the ultrasonic probe to the data processing unit is, for example, part of a PCIe connection. In particular, the data connection is implemented by a cable. The PCIe connection enables a direct memory access (DMA) to the receiving memory and the transmission memory. Via one and the same PCIe connection, actuation data can be transferred in one direction and at the same time measurement data can be transferred in the other direction, as can additional data packets, in particular the already mentioned message data packets (MSI), wherein, in a preferred embodiment, the data volume of the message data packets (MSI) is at least two orders of magnitude less than the volume of the data managed via the ring memories.

During the operation of the ultrasonic system, in a preferred process management by a central program, two secondary processes are started. One of these processes fills the transmission memory; the other process issues reconstruction commands to the additional processor, in particular graphics processor. Two different message data packets (MSI) are attached to a file system in such a manner that counting semaphores are implemented. These semaphores are periodically read by the two processes, whereby, on the one hand, the writing into the transmission memory is blocked as long as the ultrasonic probe does not remove sufficient data from the transmission memory, and, on the other hand, the removal of data from the receiving memory is blocked as long as the ultrasonic probe has not written sufficient data into the receiving memory. By means of these need-based blockades, a synchronization is implemented in the order of magnitude of a 1 ms level, which is sufficiently fast for a fluidly perceived monitor display. The merely rudimentary data processing within the ultrasonic probe on a 10 ps level in terms of order of magnitude, which meets hard real-time requirements, should be differentiated from the 1 ms level which can be reached by means of the standard operating system. The real-time bus system (RTS) lying between these two extremes enables the bidirectional transfer of sufficiently large data streams between the ultrasonic probe and the data processing unit, wherein the measurement data supplied by the ultrasonic probe, with the exception of the digitization, is transferred unprocessed.

The ultrasonic probe, as active probe, in contrast to the prior art, is capable of first automatically requesting data necessary for operating the transmitting and receiving elements from the transmission memory to be included in the data processing device and of using said data within the real-time bus system (RTS), and secondly of automatically writing measurement data in the receiving memory to be included in the data processing device.

BRIEF DESCRIPTION OF THE DRAWINGS

Below, an embodiment example of the invention is explained in further detail in reference to a drawing. In the drawing.

DETAILED DESCRIPTION OF THE PREFERRED EMBODIMENT

An ultrasonic system overall designated by 1 comprises an ultrasonic probe 2 and a data processing unit 3 data-coupled thereto. In the operation of the ultrasonic system 1, the ultrasonic probe 2 is managed manually in a known manner by the user, that is to say the physician as a rule. The data transfer between the ultrasonic probe 2 and the data processing unit 3 which is located, for example, in a movable framework, occurs in the embodiment example via a data line 14, that is to say a cable, using the PCIe standard. In general, the cable 14 represents a data connection which, in contrast to the embodiment example, could also be implemented as optical signal transfer or as radio connection.

Figure 1:
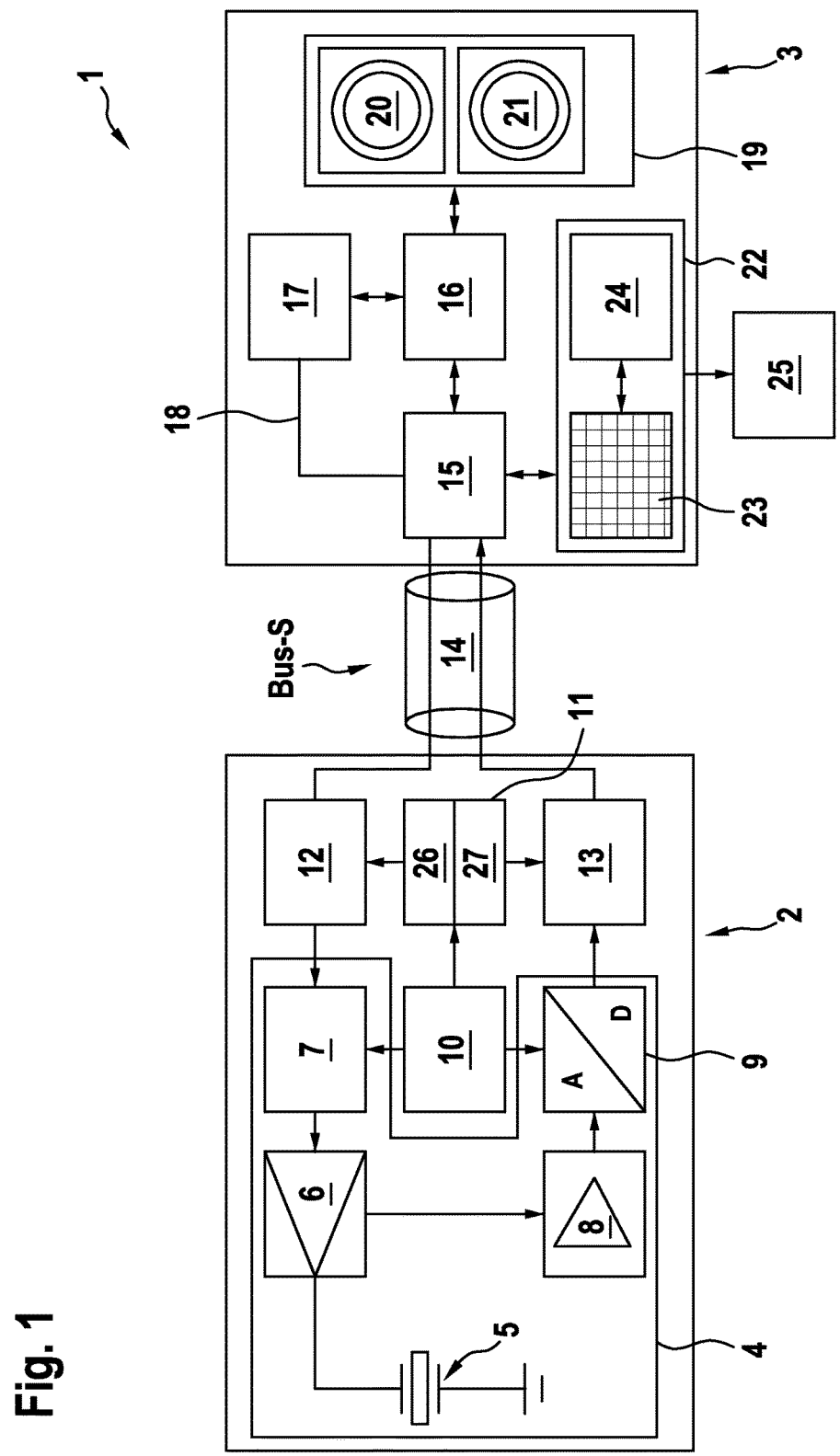
FIG. 1 shows an ultrasonic system in a diagrammatic overview.

Within the ultrasonic probe 2 which is designed as active, stateless ultrasonic probe head, a number of analog front-end units 4 are located, wherein the number of front-end units 4 is predetermined by the number of transmitting and receiving channels of the ultrasonic probe 2. A transmitting and receiving element 5, that is to say a sound transducer element, within the front-end unit 4 is constructed in a known manner as piezo element. The sound transducer element 5 is connected to a duplexer 6. The duplexer 6 in turn is linked, on the one hand, to a power transmitter 7 which is also referred to as transmission end stage, and, on the other hand, to a preamplifier 8. In the embodiment example, the transmission end stage 7 is implemented together with the duplexer 6 by a single component. Analog signals supplied by the preamplifier 8 are converted by an analog-digital converter 9 into digital signals, that is to say received signals. In a manner similar to the combined component 7, 8, in the embodiment example, the function of the preamplifier 8 and of the analog-digital converter 9 is combined to form a single component 8, 9. In general, the separation of the functional elements of the ultrasonic probe 2, on the one hand, and, of the data processing unit 3, on the other hand, as sketched in FIG. 1, is used for visualization. In fact, within the ultrasonic probe 2 as well as within the data processing unit 3, combinations of functional elements are possible in each case.

For the clocking of the data processing, within the ultrasonic probe 2, a clock generator (clock) 10, also referred to as clock for short, is provided. The clock 10 is located outside of the analog front-end 4, wherein the clock is data-linked both to the power transmitters 7 and to the analog-digital converters 9. Beyond this, data links exist between the power transmitters 7 and a transmission serializer 12, as well as between the analog-digital converters 9 and a received data packetizer 13. The transmission serializer 12 converts transmission data into channel-wise streamed bit streams clocked with constant rate for the actuation of the duplexers 6 and of the sound transducer elements 5. Conversely, the received data packetizer 13 brings about a streaming of the ADC data received from the analog-digital converters 9 in the form of received data packets.

The transmission serializer 12 just like the received data packetizer 13 is connected to a counter arrangement 11 which comprises two ring buffer address counters 26, 27, specifically a transmitting branch 26 and a receiving branch 27. The transmitting branch 26 initiates data packet requests (TLPs=transaction layer packet) to a root complex 15 for reading from a transmission data memory 20, that is to say transmission memory, which will be discussed in greater detail below. In a basically similar manner, the receiving branch 27 initiates the transmission of data packets to a received data memory 21, referred to as receiving memory for short. The counter arrangement 11, the transmission serializer 12 and the received data packetizer 13 in combination are referred to as digital connection components of the ultrasonic probe 2. The transmission data memory 20 just like the received data memory 21 is constructed as ring buffer and is to be included in a central memory 19 of the data processing unit 3. The root complex 15 is also located in the data processing unit 3.

The connection between the ultrasonic probe 2 and the data processing unit 3 is established by a bus system Bus-S which is implemented as PCIe system and comprises the cable 14. By the cable 14, that is to say PCIe cable, a bidirectional digital data connection is established. Via this data connection, during the operation of the ultrasonic system 1, data is transferred with high rates in both directions at the same time, as will be explained in further detail below.

The root complex 15 connected to the cable 14 is connected within the data processing unit 3 to a central processor (CPU) 17, to a memory management unit (MNU) 16, as well as to a graphics processor 22. From the root complex 15, signal data 18 is transferred directly, bypassing the memory management unit 16, to the central processor 17. In the present case, the signal data 18 consists of message signaled interrupts (MSI) as message data packets extracted from the root complex 15. The MSI 18 are used for notifying address counter readings of the transmitting branch 26 as well as of the receiving branch 27. When established limits are exceeded, with regard to the data transferred via the transmission serializer 12 and the received data packetizer (13) and the data removed from the transmission memory 20 or written into the receiving memory 21, the values of counters are changed. With these counters which, in a preferred design, can assume values greater than 1 and function as counting semaphores, not only is the filling and emptying of the ring buffers 20, 21 controlled, but crucially the interaction between the central processor 17 and the graphics processor 22 is also influenced.

The graphics processor 22 which in general is also referred to as processor comprises a plurality of arithmetic units 23, for example, 4096, as well as a memory unit 24. With the aid of graphics processor 22, a display device 25, specifically a monitor which can be synchronized to the image output rate, is operated. The components 15, 16, 17, 19, 22 of the data processing unit 3 together form a computation unit.

Figure 2:
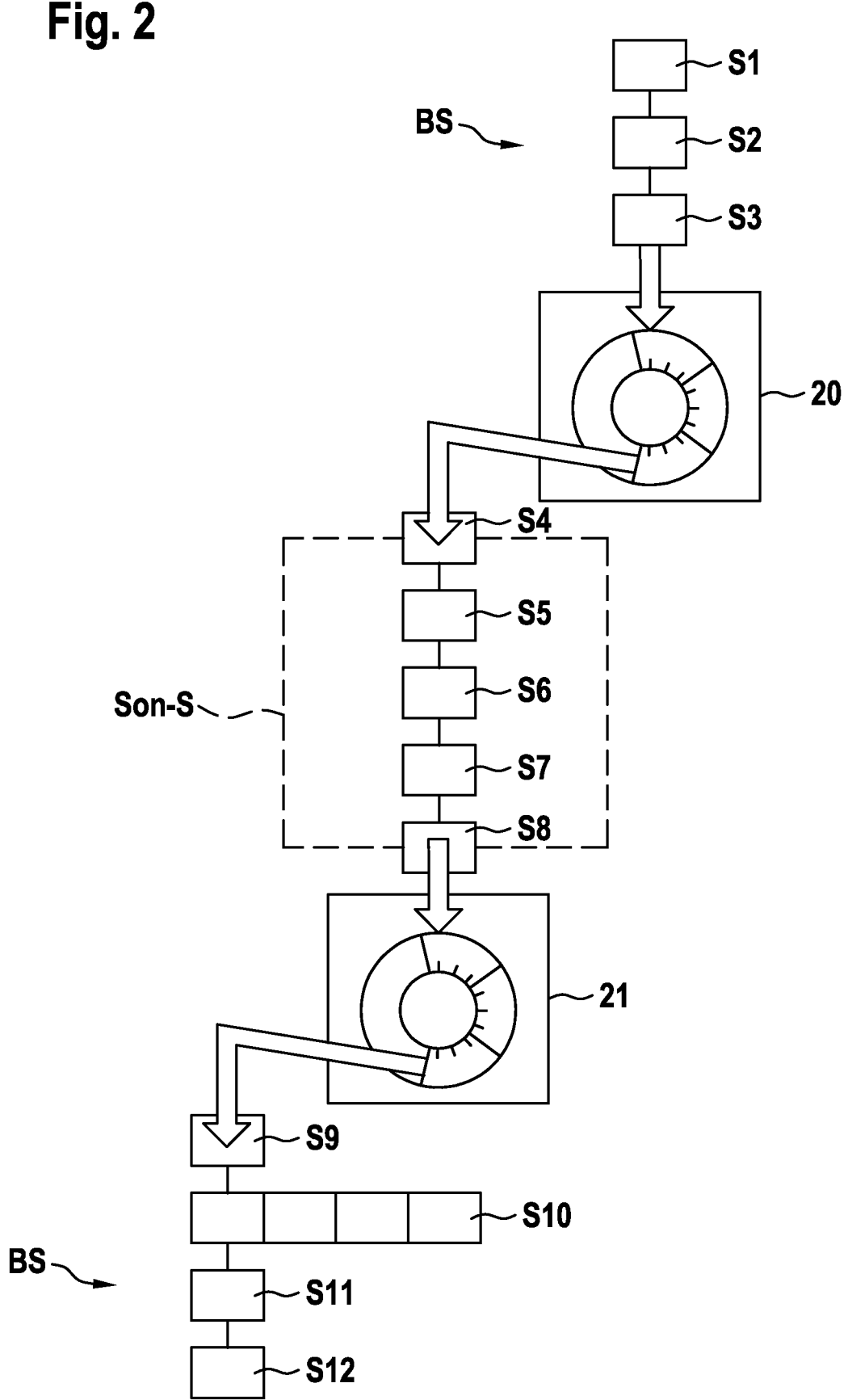
FIG. 2 shows in a diagram a method which can be carried out with the ultrasonic system according to FIG. 1.

The method which can be carried out with the ultrasonic system 1 according to FIG. 1 is illustrated in FIG. 2. Herein, a total of twelve method steps are designated by S1 to S12.

Step S1, that is to say the start of the method, is to be understood to mean the provision of the ultrasonic probe 2 and of the data processing unit 3 connected to said ultrasonic probe via a real-time bus system BUS-S. The data processing unit 3 is operated with a known standard operating system BS, referred to for short as operating system. The operating system BS has typical response times on the order of magnitude from 1 ms to 10 ms and thus does not meet hard real-time requirements. The operating system BS is also referred to as 1 ms domain. In the operating system BS, in step S2, actuation data is generated, which in the end is needed for actuating the sound transducer elements 5. The actuation data is written in step S3 into the transmission memory 20. In contrast to the central processor 17, the transmission memory 20, just like the receiving memory 21, is to be included in the real-time bus system BUS-S.

In step S4, actuation data, triggered by the ultrasonic probe 2, is read from the transmission memory 20 and transferred via the cable 14, that is to say the data connection 14, to the ultrasonic probe 2. The real-time bus system BUS-S which is constructed with the aid of the cable 14 and of the root complex 15 works with a jitter on the order of magnitude of 10 ms and is accordingly referred to as 10 ms domain.

The data read from the transmission memory 20 is transmitted by streaming, practically uninterrupted and with constant data rate, to the stateless ultrasonic probe 2. In the ultrasonic probe 2, by the clock generator 10, an 8 ns clock pulse is predetermined, wherein the clock inaccuracy is on the order of magnitude of 10 ps. The corresponding time domain in the probe system (Son-S) accordingly represents a 10 ps domain.

In step S5, using the streamed actuation data, ultrasonic pulses are generated by the transmitting and receiving elements 5, and echoes are received by the same elements 5. The received echoes are amplified in step S6 with the aid of the preamplifier 8 with constant amplification (gain). The digitization by the analog-digital converter 9 occurs in step S7.

The digitized data is transferred in step S8 by streaming via the cable 14 and written into the transmission memory 21. The transfer of data via the cable 14 to the data processing unit 3 occurs at the same time as the reception of data by the ultrasonic probe 2 from the data processing unit 3.

Asynchronously with respect to the transfer process, in step S9, data is read from the receiving memory 21 and distributed in step S10 over the arithmetic units 23. The generation of partial images in step S11 by the arithmetic units 23 represents a beam forming. The final image generation (image forming), that is to say the assembly of the ultrasonic image, occurs in step S12.

The time span from the reception of the ultrasonic echo by the sound transducer elements 5 to the output of the ultrasonic images on the display device 25 is less than 100 ms, so that the user is given the impression of viewing real-time images. In fact, the data processing, in the described manner, passes overall through passes through a total of three time domains, wherein in the time domain with the lowest clock inaccuracy, that is to say in the probe system Son-S, the data processing is reduced to a minimum, but a very high data rate of several Gbit per second is present.

Data with such a high rate is here both received by the ultrasonic probe 2 and transmitted by the ultrasonic probe 2. The volume of data received per time unit differs from the volume of data transmitted per unit of time by no more than a factor of five. The very high rate of data received by the ultrasonic probe 2 is directly connected with the stateless operation of the ultrasonic probe 2. The cable 14 used for the bidirectional data transfer in fact has a clock inaccuracy which fails to reach the precision of the probe system Son-S by several orders of magnitude, but in comparison to the standard operating system BS it meets relatively high real-time requirements.

The entire process of beam forming is shifted into the data processing unit 3 which runs on the operating system BS. This means, inter alia, that, during the triggering of a single so-called shot by the ultrasonic probe 2, that is to say during the generation of an ultrasonic signal, the echo of which is to be evaluated, not only is a small partial region, that is to say one or fewer image columns, viewed, as is conventional in the prior art, but also all the data to be physically associated with a transmission pulse is received and transferred, specifically streamed, without digital processing. It is only within the data processing unit 3 that, from the received data, partial quantities are extracted, which are used for generating partial images and in the end a complete image.

LIST OF REFERENCE NUMERALS

1 Ultrasonic system
2 Ultrasonic probe
3 Data processing unit
4 Analog front-end
5 Transmitting and receiving element, sound transducer element
6 Duplexer
7 Power transmitter, transmitter end stage
8 Preamplifier
9 Analog-digital converter
10 Clock generator, clock
11 Counter arrangement
12 Transmission serializer
13 Received data packetizer
14 Data connection, cable
15 Root complex
16 Memory management unit
17 Central processor, CPU
18 MSI data packet, signal data
19 Central memory
20 Transmission memory, ring memory
21 Receiving memory, ring memory
22 Processor, graphics processor
23 Arithmetic unit
24 Memory
25 Display device
26 Transmitting branch of the counter arrangement
27 Receiving branch of the counter arrangement
BS Operating system, standard operating system
Bus-S Real-time bus system
Son-S Probe system
S1 . . . S12 Method steps

The invention claimed is:
1. An ultrasonic system, with an ultrasonic probe; the ultrasonic system comprising:
   a plurality of transmitting and receiving elements,
   a data processing unit which is physically separate from the ultrasonic probe and connected to said ultrasonic probe by data connection,
   wherein the ultrasonic probe has a plurality of analog preamplifiers, a plurality of analog-digital converters and at least one digital connection component, the data processing unit has two ring memories, the ring memories comprising a receiving memory and a transmission memory, a computation unit configured for generating ultrasonic images, and wherein, for data coupling of the ultrasonic probe to the computation unit, a real-time bus system comprising the data connection is provided, in which the ring memories are incorporated and which is connected to a probe system managing data within the ultrasonic probe, and an operating system for operating the computation unit, and wherein a clock inaccuracy of the probe system is at least three orders of magnitude less and a response time of the operating system is at least two orders of magnitude longer than a clock inaccuracy of the real-time bus system, and wherein the real-time bus system in cooperation with the probe system and with the operating system is configured to transfer transmission data and received data simultaneously by uninterrupted streaming clocked with an on average constant rate during stateless operation of the ultrasonic probe, said stateless operation not differentiating between transmission and receiving operation.

2. The ultrasonic system according to claim 1, wherein by the data connection, a connection is established between the ultrasonic probe and a root complex which is integrated in the data processing unit, which is provided for transfer of message data packets relating to transmission data and to received data, wherein, by the message data packets, counting semaphores are implemented for temporarily blocking and releasing streaming data transfer into the transmission memory and out of the receiving memory.

3. The ultrasonic system according to claim 2, wherein upstream of each transmitting and receiving element, a duplexer is connected, which is configured for clocked application of one of n codes to the transmitting and receiving element for in each case exactly one clock pulse, wherein n is at least four, and (n−1) transmission codes and exactly one reception code are provided.

4. The ultrasonic system according to claim 2, wherein a data transfer capacity kept available for transferring message data packets is not more than, in each case, 1% of the data transfer capacities provided for transferring actuation data, and measurement data via the data connection.

5. The ultrasonic system according to claim 1, wherein between temporal jitter of the probe system, jitter of the real-time bus system, and the response time of the operating system, the following relationship exists:

$$10^1 \le \frac{TBus^2}{TSoN * TBS} \le 10^4.$$

6. The ultrasonic system according to claim 1, wherein the receiving memory is configured to store received data blocks which are associated with transmission data sets, for at least 20 ms.

7. The ultrasonic system according to claim 6, wherein the transmission data stream is provided for continuous, uninterrupted actuation of the transmitting and receiving elements, and associated received data stored in the transmission and receiving memories is stored temporally uninterrupted, sequentially, and without an associated time signal in each individual case.

8. The ultrasonic system according to claim 1, wherein the data connection between the ultrasonic probe and the ring memories is configured as a PCIe connection.

9. The ultrasonic system according to claim 8, wherein the data connection comprises a cable connecting the ultrasonic probe to the data processing unit.

10. An imaging ultrasonic method, wherein an object to be examined is exposed to ultrasonic pulses and echo signals are received, having the following features:

providing an ultrasonic probe which comprises a plurality of transmitting and receiving elements, and of a data processing unit data-coupled to said ultrasonic probe, which comprises a central processor and a processor, generating actuation data for operating the transmitting and receiving elements, by the data processing unit, wherein the actuation data is generated on a standard operating system which does not meet any hard real-time requirements, and is written asynchronously—with respect to the generation—in a transmission memory configured as memory which is to be included in a real-time bus system, asynchronous—with respect to the generation and the storage of the actuation data—transmitting of actuation data from the transmission memory to the ultrasonic probe, wherein the ultrasonic probe is operated as a component of the real-time bus system and the actuation data is transmitted with an on average constant first data transfer rate without pause by streaming, and wherein clock inaccuracy of a probe system comprising components within the ultrasonic probe is at least three orders of magnitude less and response time of the standard operating system is at least two orders of magnitude longer than clock inaccuracy of the real-time bus system, generating ultrasonic pulses in accordance with the actuation data with the aid of transmission end stages arranged in the ultrasonic probe, wherein the transmitting and receiving elements actuated by the transmission end stages are configured as piezo elements, analog amplifying and synchronously digitizing the associated echo signals in the ultrasonic probe without interruption and with constant clock frequency, and asynchronously written by streaming in real time, uninterrupted, without further processing, via a data connection into a receiving memory which is to be included in the real-time bus system and which is spatially separate from the ultrasonic probe and configured as ring memory, wherein data transfer to the receiving memory occurs uninterrupted with an substantially constant second data transfer rate which deviates by no more than a factor of five from the first data transfer rate relating to the data transfer from the data processing unit to the ultrasonic probe, a selection of data received in the receiving memory is distributed, controlled by the central processor, as measurement data blocks over multiple arithmetic units, wherein the individual measurement data blocks in each case are associated with a group of receiving elements, processing multiple measurement data sets in parallel and asynchronously with respect to the writing into the receiving memory, of the real-time bus system, by arithmetic units which are controlled in each case by the central processor running on the standard operating system, wherein the processing in each case comprises a received beam forming and image reconstruction, and a partial image is reconstructed with the aid of each arithmetic unit, generating from the partial images, an overall image by the data processing unit as ultrasonic image.

11. The ultrasonic method according to claim 10, wherein, in addition to actuation data and measurement data supplied by the ultrasonic probe, within the data processing unit, message data packets are transferred, which implement counting semaphores for blocking and releasing streaming serial data transfer into the transmission memory and out of the receiving memory, wherein a data volume of the message data packets is at least two orders of magnitude less than a volume of the data managed via the ring memories.

12. The ultrasonic method according to claim 10, wherein the echo signals of each receiving channel are analog amplified within the ultrasonic probe with constant amplification by a preamplifier.

13. The ultrasonic method according to claim 10, wherein data without explicit time information is written into the transmission memory and receiving memory, wherein the time information, when the data is read out, is implicitly obtained from a size of the stored data blocks and from a sequence of the storage address.

14. The ultrasonic method according to claim 10, wherein, first, the ultrasonic probe automatically requests from the transmission memory data necessary for operating the transmitting and receiving elements and uses said data within the real-time bus system, and, second, the ultrasonic probe automatically writes measurement data into the receiving memory.

15. The ultrasonic method according to claim 10, wherein the ultrasonic probe automatically assumes a safe default state during the switching on and during breaking of the connection to the data processing unit.

16. The ultrasonic method according to claim 10, wherein the processor comprises a graphics processor with a plurality of arithmetic units.

\* \* \* \* \*